US012029862B2

(12) United States Patent
Govari et al.

(10) Patent No.: US 12,029,862 B2
(45) Date of Patent: Jul. 9, 2024

(54) EXPANDABLE ASSEMBLY CATHETER

(71) Applicant: Biosense Webster (Israel) Ltd., Yokneam (IL)

(72) Inventors: Assaf Govari, Haifa (IL); Christopher Thomas Beeckler, Brea, CA (US); Joseph Thomas Keyes, Sierra Madre, CA (US); Kevin Justin Herrera, West Covina, CA (US); Alexander David Squires, Duarte, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 344 days.

(21) Appl. No.: 16/723,971

(22) Filed: Dec. 20, 2019

(65) Prior Publication Data
US 2021/0187241 A1    Jun. 24, 2021

(51) Int. Cl.
*A61M 25/00*    (2006.01)
*A61B 5/00*    (2006.01)
(Continued)

(52) U.S. Cl.
CPC ......... *A61M 25/0023* (2013.01); *A61B 5/287* (2021.01); *A61B 5/6858* (2013.01);
(Continued)

(58) Field of Classification Search
CPC ..... A61B 5/287; A61B 5/6858; A61B 5/6859; A61B 5/367; A61M 25/0141
See application file for complete search history.

(56) References Cited

U.S. PATENT DOCUMENTS 5,313,943 A * 5/1994 Houser ................ A61B 5/6858
                                                        600/374
5,391,199 A    2/1995 Ben-Haim
(Continued)

FOREIGN PATENT DOCUMENTS

EP    2848226 A1    3/2015
EP    3335626 A1    6/2018
(Continued)

OTHER PUBLICATIONS

Extended European Search Report dated May 18, 2021, for Application No. 20215568.5, 9 pages.
(Continued)

*Primary Examiner* — Brandy S Lee
(74) *Attorney, Agent, or Firm* — FROST BROWN TODD LLP

(57) ABSTRACT

One embodiment includes a catheter apparatus, including an elongated deflectable element including a distal end, a coupler connected to the distal end, a pusher including a distal portion, and configured to be advanced and retracted through the deflectable element, a nose connector connected to the distal portion, and including a distal receptacle having an inner surface and a distal facing opening, and an expandable assembly including flexible polymer circuit strips, each strip including electrodes disposed thereon, the strips being disposed circumferentially around the distal portion of the pusher, with first ends of the strips being connected to the coupler and second ends of the strips including respective hinges entering the distal facing opening and connected to the inner surface of the distal receptacle, the strips being configured to bow radially outward when the pusher is retracted expanding the expandable assembly from a collapsed form to an expanded form.

17 Claims, 14 Drawing Sheets

(51) Int. Cl.
*A61B 5/287* (2021.01)
*A61B 5/367* (2021.01)
*A61M 25/01* (2006.01)

(52) U.S. Cl.
CPC .... *A61M 25/0141* (2013.01); *A61M 25/0158* (2013.01); *A61B 5/367* (2021.01); *A61B 2562/00* (2013.01); *A61B 2562/164* (2013.01); *A61M 2025/0024* (2013.01)

(56) References Cited

U.S. PATENT DOCUMENTS

| | | | |
|---|---|---|---|
| 5,823,189 | A | 10/1998 | Kordis |
| 5,967,977 | A * | 10/1999 | Mullis ................. A61N 1/0517 600/380 |
| 6,239,724 | B1 | 5/2001 | Doron et al. |
| 6,332,089 | B1 | 12/2001 | Acker et al. |
| 6,484,118 | B1 | 11/2002 | Govari |
| 6,618,612 | B1 | 9/2003 | Acker et al. |
| 6,690,963 | B2 | 2/2004 | Ben-Haim et al. |
| 8,644,902 | B2 | 2/2014 | Kordis et al. |
| 9,339,331 | B2 * | 5/2016 | Tegg ................. A61B 18/1492 |
| 2002/0065455 | A1 | 5/2002 | Ben-Haim et al. |
| 2003/0120150 | A1 | 6/2003 | Govari |
| 2004/0068178 | A1 | 4/2004 | Govari |
| 2009/0171274 | A1 * | 7/2009 | Harlev ............. A61M 25/0147 604/95.04 |
| 2012/0239028 | A1 | 9/2012 | Wallace et al. |
| 2012/0271135 | A1 * | 10/2012 | Burke ................. A61B 5/6858 600/373 |
| 2013/0253298 | A1 | 9/2013 | Harlev et al. |
| 2015/0080693 | A1 * | 3/2015 | Solis ................. A61B 18/1492 600/374 |
| 2015/0314127 | A1 | 11/2015 | Zarius et al. |
| 2017/0332970 | A1 * | 11/2017 | Aujla ................. A61B 5/6858 |
| 2018/0168511 | A1 * | 6/2018 | Hall ................. A61M 25/0074 |
| 2018/0184982 | A1 * | 7/2018 | Basu ................. A61B 5/6858 |
| 2019/0021620 | A1 | 1/2019 | Olson et al. |
| 2020/0138512 | A1 | 5/2020 | Beeckler et al. |
| 2020/0178897 | A1 * | 6/2020 | Osypka ................. A61B 5/287 |
| 2020/0337765 | A1 | 10/2020 | Smith |
| 2021/0187241 | A1 | 6/2021 | Govari et al. |
| 2022/0054192 | A1 | 2/2022 | Beeckler et al. |

FOREIGN PATENT DOCUMENTS

| | | |
|---|---|---|
| WO | WO 96/05768 A1 | 2/1996 |
| WO | WO 2016/183247 A1 | 11/2016 |

OTHER PUBLICATIONS

Partial European Search Report dated Mar. 7, 2023, for Application No. 22210328.5, 14 pages.

Extended European Search Report dated Jun. 7, 2023, for Application No. 22210328.5, 13 pages.

* cited by examiner

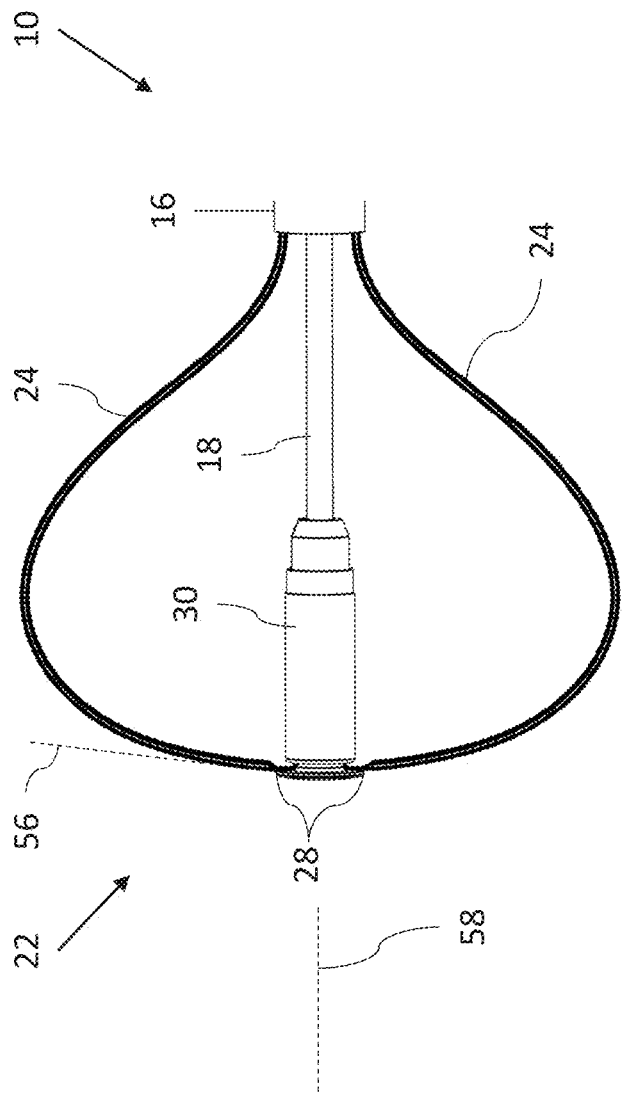
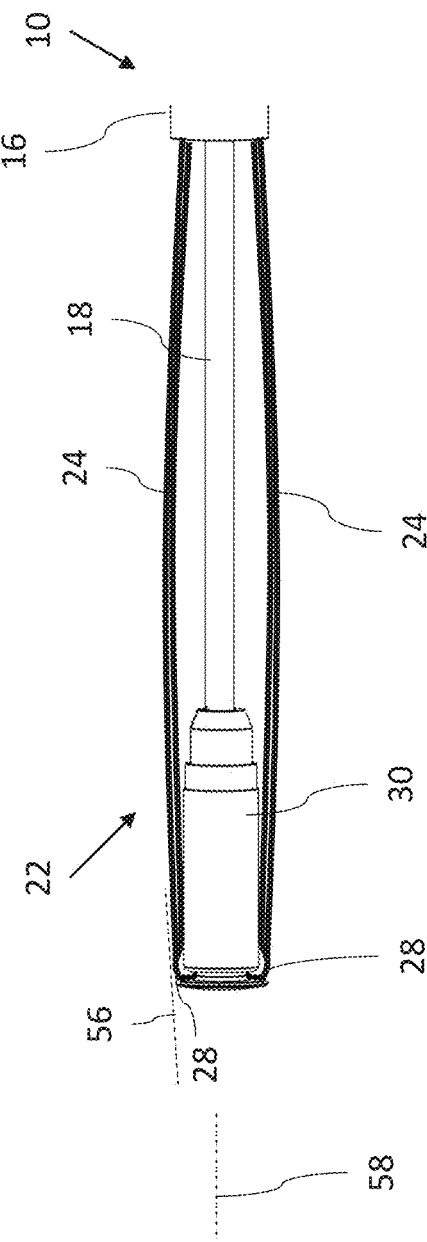
FIG. 6A
FIG. 6B

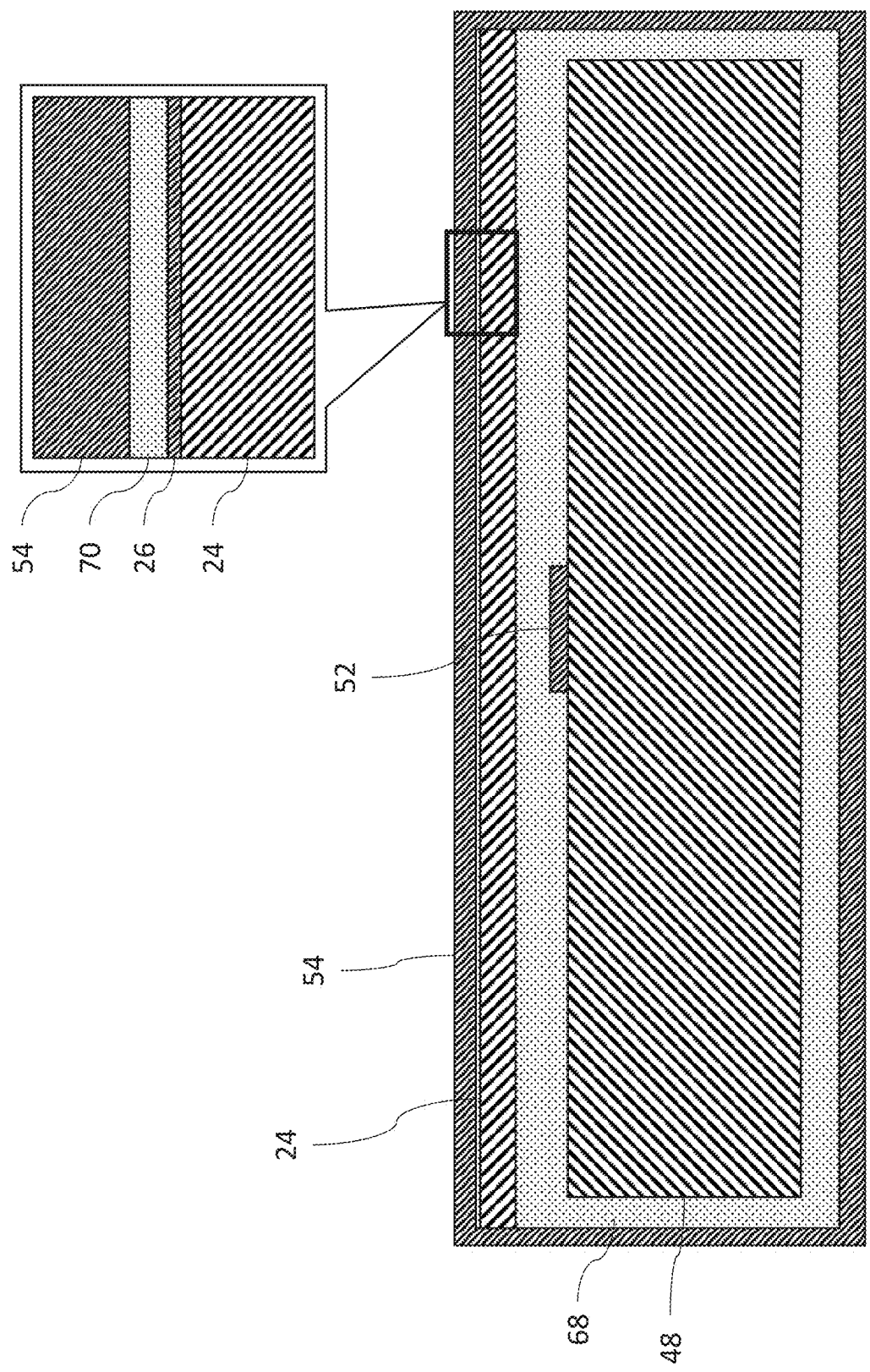

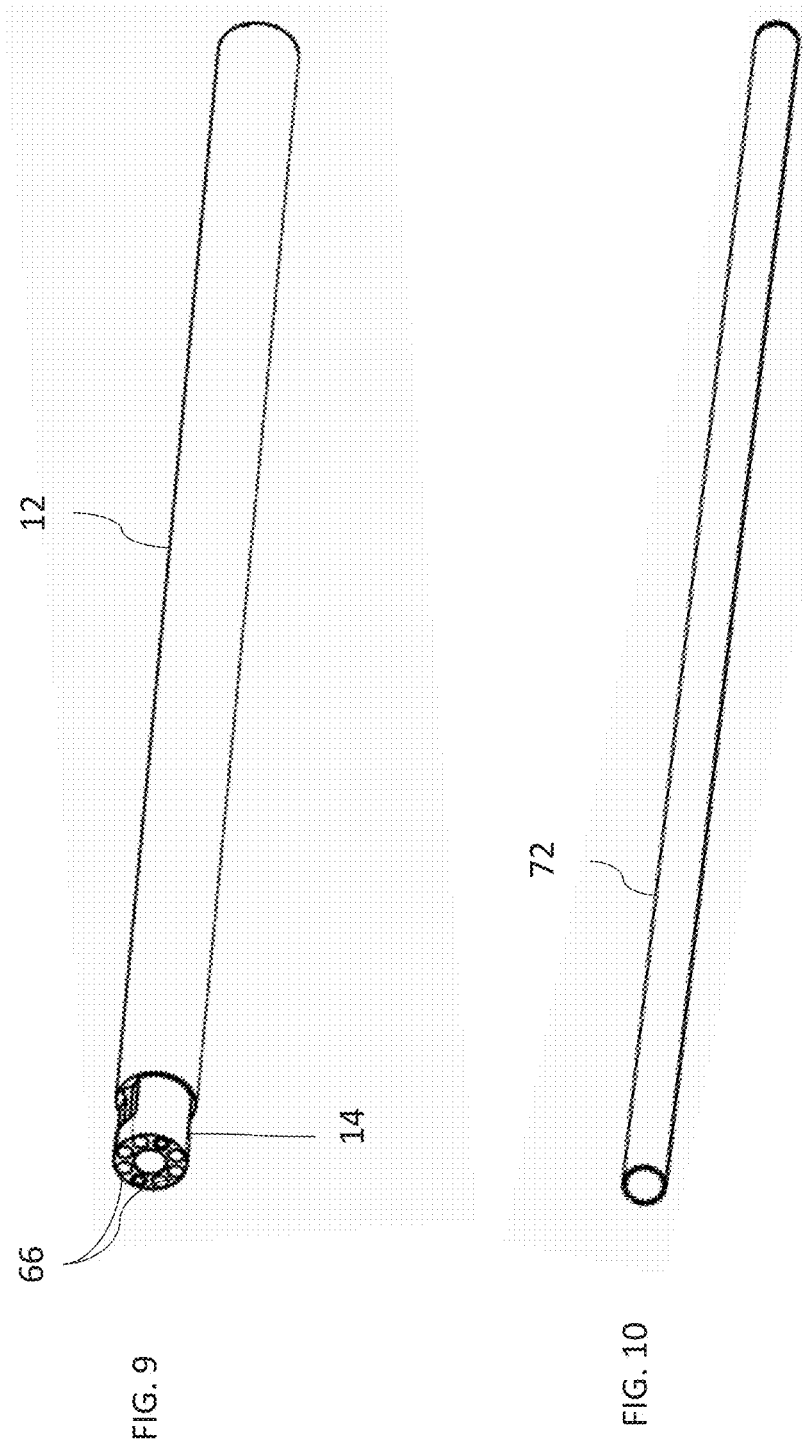

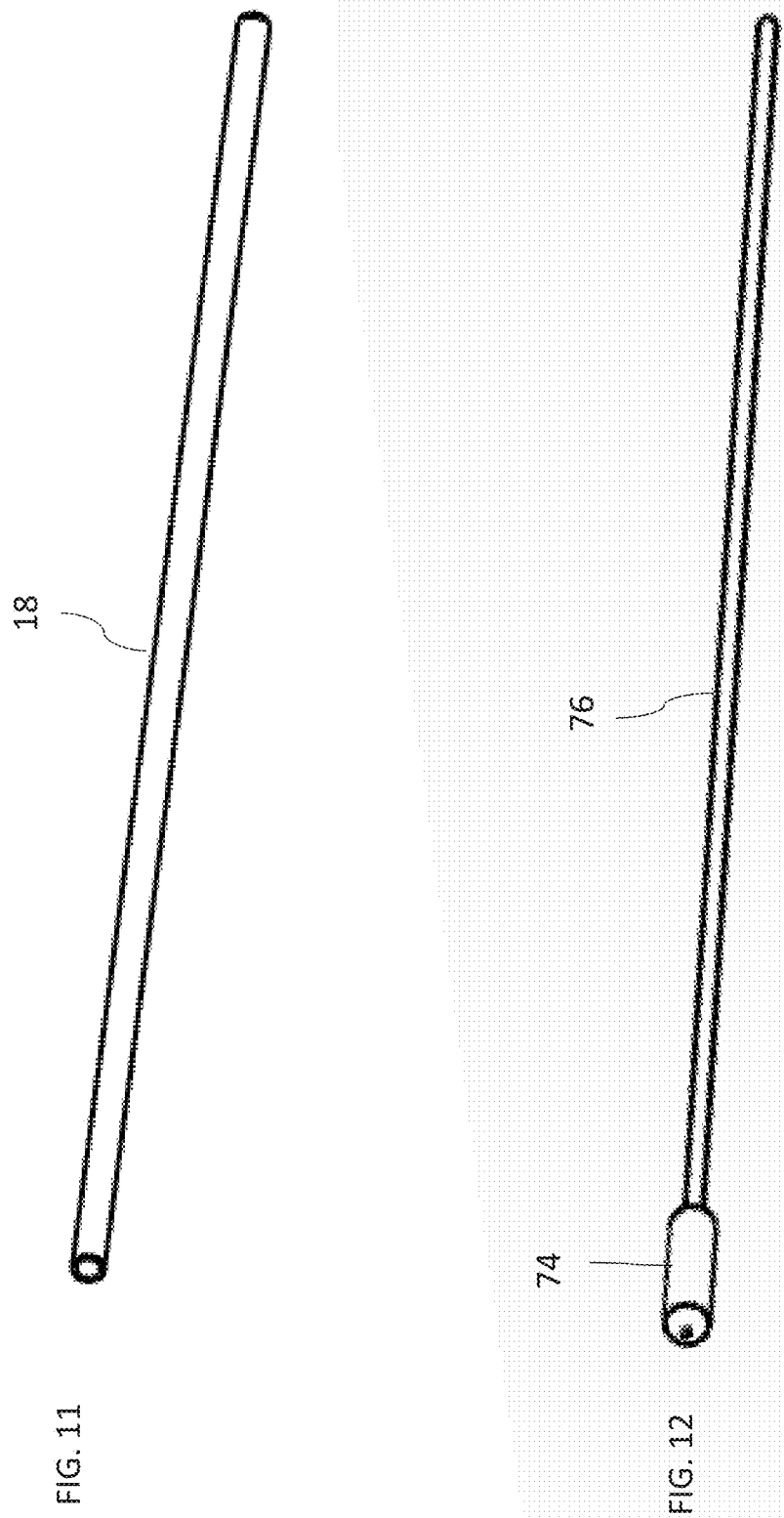

EXPANDABLE ASSEMBLY CATHETER

FIELD OF THE INVENTION

The present invention relates to medical equipment, and in particular, but not exclusively, to expandable assembly catheters.

BACKGROUND

A wide range of medical procedures involve placing probes, such as catheters, within a patient's body. Location sensing systems have been developed for tracking such probes. Magnetic location sensing is one of the methods known in the art. In magnetic location sensing, magnetic field generators are typically placed at known locations external to the patient. A magnetic field sensor within the distal end of the probe generates electrical signals in response to these magnetic fields, which are processed to determine the coordinate locations of the distal end of the probe. These methods and systems are described in U.S. Pat. Nos. 5,391,199, 6,690,963, 6,484,118, 6,239,724, 6,618,612 and 6,332,089, in PCT International Publication No. WO 1996/005768, and in U.S. Patent Application Publications Nos. 2002/006455 and 2003/0120150 and 2004/0068178. Locations may also be tracked using impedance or current based systems.

One medical procedure in which these types of probes or catheters have proved extremely useful is in the treatment of cardiac arrhythmias. Cardiac arrhythmias and atrial fibrillation in particular, persist as common and dangerous medical ailments, especially in the aging population.

Diagnosis and treatment of cardiac arrhythmias include mapping the electrical properties of heart tissue, especially the endocardium and the heart volume, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure, mapping followed by ablation, electrical activity at points within the heart is typically sensed and measured by advancing a catheter containing one or more electrical sensors into the heart, and acquiring data at a multiplicity of points. These data are then utilized to select the endocardial target areas at which the ablation is to be performed.

Electrode catheters have been in common use in medical practice for many years. They are used to stimulate and map electrical activity in the heart and to ablate sites of aberrant electrical activity. In use, the electrode catheter is inserted into a major vein or artery, e.g., femoral vein, and then guided into the chamber of the heart of concern. A typical ablation procedure involves the insertion of a catheter having a one or more electrodes at its distal end into a heart chamber. A reference electrode may be provided, generally taped to the skin of the patient or by means of a second catheter that is positioned in or near the heart. RF (radio frequency) current is applied to the tip electrode(s) of the ablating catheter, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive.

US Patent Publication 2013/0253298 of Harley, et al., describes a multi electrode catheter for non-contact mapping of the heart having independent articulation and deployment features.

US Patent Publication 2012/0239028 of Wallace, et al., describes in one embodiment, a device including an expandable support member having a first portion and a second portion. The first portion is adapted to have a smaller expansion index than the second portion. A therapeutic or diagnostic instrument is supported, at least in part, by the expandable support member first portion. In another embodiment, the support member is adapted for non-uniform expansion of the first and second portions. There are also described methods of forming therapeutic devices. There are also described methods of providing therapy to tissue in a body by positioning a device in proximity to tissue in a body selected to receive therapy. Next, the expandable support member second portion is expanded until the instrument is at a therapeutic position relative to the tissue in a body selected to receive therapy. Thereafter, therapy or diagnosis is provided to the selected tissue using the device.

U.S. Pat. No. 5,823,189 to Kordis describes an electrode support structure has at least two spline leaves, each comprising an opposed pair of spline elements connected by a center web. Each web has a hole through which a pin assembly extends to join the webs of the spline leaves in a mutually stacked relationship. The spline elements radiate from the pin assembly in a circumferentially spaced relationship for carrying one or more electrodes. A hub member is over-molded about the pin assembly.

U.S. Pat. No. 8,644,902 to Kordis, et al., describes a method for sensing multiple local electric voltages from endocardial surface of a heart, and includes providing a system for sensing multiple local electric voltages from endocardial surface of a heart, including: a first elongate tubular member having a lumen, a proximal end and a distal end; a basket assembly including: a plurality of flexible splines for guiding a plurality of exposed electrodes, the splines having proximal portions, distal portions and medial portions therein between, wherein the electrodes are substantially flat electrodes and are substantially unidirectionally oriented towards a direction outside of the basket.

SUMMARY

There is provided in accordance with an embodiment of the present disclosure, a catheter apparatus, including an elongated deflectable element including a distal end, a coupler connected to the distal end, a pusher including a distal portion, and being configured to be advanced and retracted through the deflectable element, a nose connector connected to the distal portion of the pusher, and including a distal receptacle having an inner surface and a distal facing opening, and an expandable assembly including a plurality of flexible polymer circuit strips, each flexible polymer circuit strip including multiple electrodes disposed thereon, the flexible polymer circuit strips being disposed circumferentially around the distal portion of the pusher, with first ends of the strips being connected to the coupler and second ends of the strips including respective hinges entering the distal facing opening and connected to the inner surface of the distal receptacle of the nose connector, the strips being configured to bow radially outward when the pusher is retracted expanding the expandable assembly from a collapsed form to an expanded form.

Further in accordance with an embodiment of the present disclosure the respective hinges are configured to provide a maximum angular range of movement, which is in excess of 80 degrees, between the collapsed form and the expanded form.

Still further in accordance with an embodiment of the present disclosure the hinges have a thickness in the range of 10 to 140 microns.

Additionally, in accordance with an embodiment of the present disclosure, the apparatus includes respective elongated resilient support elements connected along a given length of respective ones of the flexible polymer circuit strips providing a shape of the expandable assembly in the expanded form.

Moreover, in accordance with an embodiment of the present disclosure the elongated resilient support elements include Nitinol.

Further in accordance with an embodiment of the present disclosure the elongated resilient support elements include Polyetherimide (PEI).

Still further in accordance with an embodiment of the present disclosure the respective elongated resilient support elements extend along the respective strips from the coupler until before the respective hinges.

Additionally, in accordance with an embodiment of the present disclosure the flexible polymer circuit strips include a polyimide layer.

Moreover, in accordance with an embodiment of the present disclosure the hinges of the flexible polymer circuit strips are supported with a length of yarn.

Further in accordance with an embodiment of the present disclosure the yarn includes any one or more of the following an ultra-high-molecular-weight polyethylene yarn, or a yarn spun from a liquid-crystal polymer.

Still further in accordance with an embodiment of the present disclosure the flexible polymer circuit strips are covered with a thermoplastic polymer resin shrink wrap (PET).

Additionally, in accordance with an embodiment of the present disclosure respective ones of the second ends of respective ones of the flexible polymer circuit strips are tapered along the width of the respective ones of the flexible polymer circuit strips.

Moreover, in accordance with an embodiment of the present disclosure the coupler has an inner surface, the first ends of the strips being connected to the inner surface of the coupler.

Further in accordance with an embodiment of the present disclosure respective ones of the first ends of respective ones of the flexible polymer circuit strips include an electrical connection array.

Still further in accordance with an embodiment of the present disclosure, the apparatus includes a position sensor disposed in the distal receptacle of the nose connector.

Additionally, in accordance with an embodiment of the present disclosure, the apparatus includes a position sensor disposed between the coupler and the pusher.

Moreover, in accordance with an embodiment of the present disclosure, the apparatus includes a nose cap covering the distal facing opening of the nose connector.

BRIEF DESCRIPTION OF THE DRAWINGS

The present invention will be understood from the following detailed description, taken in conjunction with the drawings in which:

FIGS. 6A and 6B are schematic views of the expandable assembly of the basket catheter of FIG. 1 in expanded and collapsed form;

FIG. 8 is a cross-sectional view through line A-A of FIG. 7;

FIG. 9 is a schematic view of a deflectable element of the basket catheter of FIG. 1;

FIG. 10 is a schematic view of an irrigation sleeve of the basket catheter of FIG. 1;

FIG. 11 is a schematic view of a pusher of the basket catheter of FIG. 1;

FIG. 12 is a schematic view of a multi-axis position sensor of the basket catheter of FIG. 1;

DESCRIPTION OF EXAMPLE EMBODIMENTS

Overview

Figure 1:
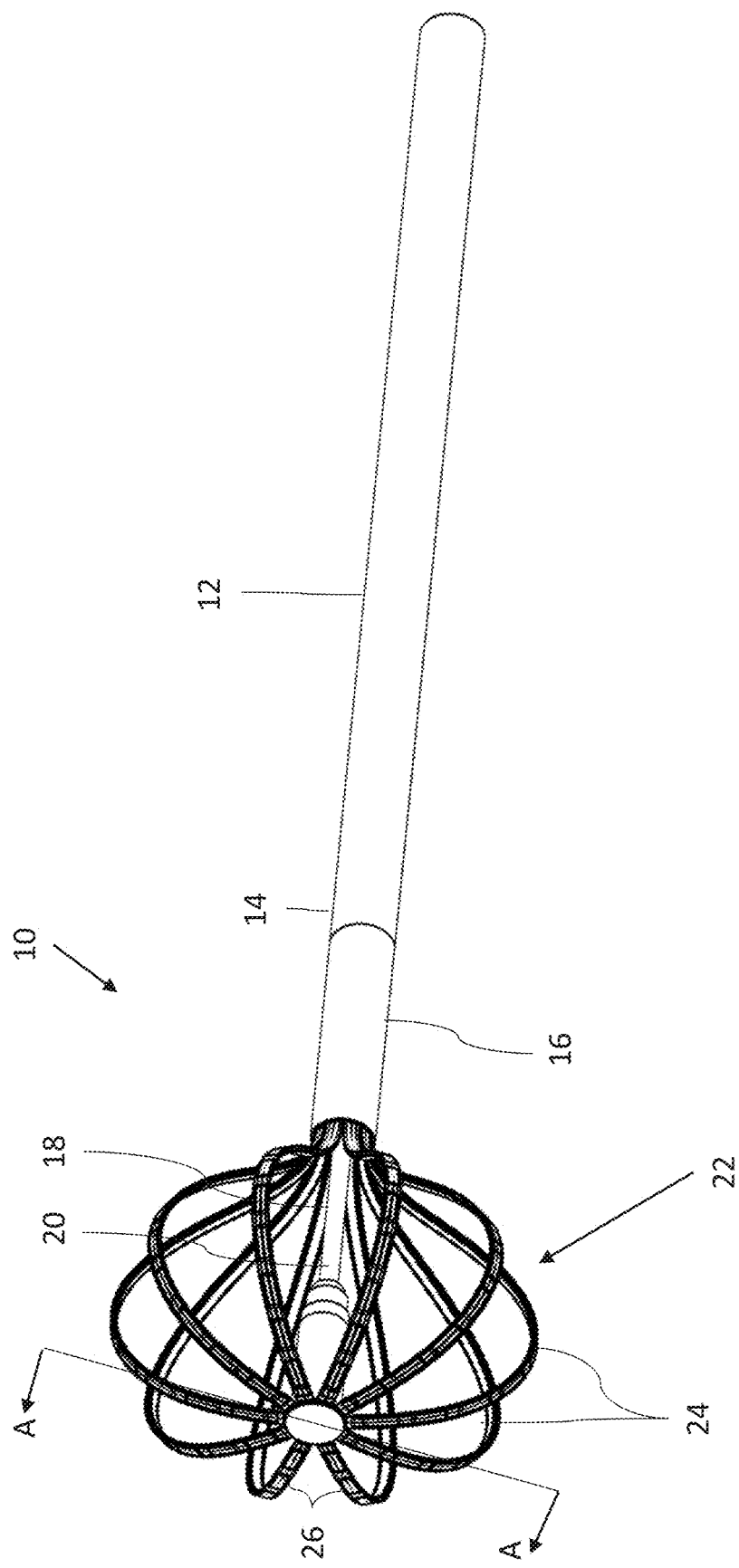
FIG. 1 is a schematic view of a basket catheter constructed and operative in accordance with an embodiment of the present invention.

Investigative electrodes on basket catheters are generally distributed along the length of the splines of the basket assembly. Proximal ends of the splines of the basket assembly are generally connected to an insertion tube of the catheter, while distal ends of the splines are connected to a pusher which is disposed within an insertion tube. The pusher may be retracted and advanced, to expand and collapse, the basket assembly, respectively. When the basket assembly is collapsed, the splines have a substantially linear formation, with the distal ends of the splines being connected to outer surface of the pusher and typically covered with a cap forming the nose of the catheter. When the basket assembly is expanded the nose of the catheter protrudes distally beyond the expanded assembly.

During investigative procedures, the tissue region contacted by the distal portion of the basket is of greater interest than other regions for investigative purposes, but due to the nose of the basket protruding beyond the expanded assembly, some of the distal portion surrounding the nose of the basket assembly is prevented from making contact with tissue thereby preventing using some of that distal portion for investigative purposes.

Basket catheters with flatter noses have been proposed, but generally these catheters suffer from various disadvantages such as the nose is not flat enough, the basket does not collapse sufficiently, and/or the structural engineering of the basket is deficient in one or more ways such that the basket fails under compression and/or tension when being deployed and/or in use.

Embodiments of the present invention solve the above problems by providing a catheter apparatus including an expandable basket assembly with a substantially flat nose so that electrodes may be placed close to the nose and still make contact with tissue when the basket assembly is expanded. The distal ends of the splines include hinges which are flexible enough and have a large enough angular range of bending to allow the expandable assembly to achieve its fully expanded form and its fully collapsed form, while being strong enough to withstand the various compressive and tensile stresses applied to the catheter. The distal ends of the splines are tucked into, and connected to, a receptacle at the end of the pusher so that the end of the catheter is either level with the basket assembly when the basket is expanded or only sticks out at minimal distance (for example, up to about 1 mm) from the expanded basket assembly.

In some embodiments, the catheter apparatus includes an elongated deflectable element, a coupler connected to the distal end of the deflectable element, and a pusher, which may be advanced and retracted through the deflectable element. The apparatus also includes a nose connector connected to the distal portion of the pusher, and an expandable assembly comprising flexible polymer circuit strips. Each flexible polymer circuit strip includes multiple electrodes disposed thereon. The flexible polymer circuit strips are placed circumferentially around the distal portion of the pusher, with first ends of the strips being connected to the coupler and second ends of the strips comprising respective hinges entering a distal facing opening of a distal receptacle of the nose connector and connected to the inner surface of the distal receptacle of the nose connector. The strips are configured to bow radially outward when the pusher is retracted expanding the expandable assembly from a collapsed form to an expanded form.

In some embodiments, the second ends of the flexible polymer circuit strips are tapered along their width to facilitate insertion of the strips into the receptacle without overlap. In some embodiments, the first ends of the strips are connected to the inner surface of the coupler.

The apparatus includes respective elongated resilient support elements connected along a given length of respective ones of the flexible polymer circuit strips providing a shape of the expandable assembly in the expanded form. The respective elongated resilient support elements extend along the respective strips from the coupler until before the respective hinges thereby providing the strips with sufficient resilience where needed without adding bulk to the hinges. The elongated resilient support elements may include any suitable resilient material, for example, but not limited to, Nitinol and/or Polyetherimide (PEI).

The flexible polymer circuit strips may include a polyimide layer. The hinges of the flexible polymer circuit strips may be strengthened with any suitable material, for example, but not limited to, a length of yarn, which is flexible and provides tensile support to the strips. In some embodiments, a length of yarn runs the whole length of each strip including the hinges. The yarn may include any suitable yarn. For example, the yarn may include one or more of the following: an ultra-high-molecular-weight polyethylene yarn; or a yarn spun from a liquid-crystal polymer. Each flexible polymer circuit strip, its length of yarn, and elongated resilient support element may be secured together with a suitable adhesive, for example, epoxy, and then covered with a thermoplastic polymer resin shrink wrap (PET) or any other suitable covering. Windows may be created in the PET covering with a laser, mechanical removal, or any other suitable method in order to expose the electrodes. Alternatively, prior to shrinking, the PET covering may already have windows present.

In some embodiments, each flexible polymer circuit strip may be electrically isolated from its elongated resilient support element, for example, by coating the elongated resilient support element with an insulator or by using a covering such as a shrink wrap which wraps the elongated resilient support element and the length of yarn. In some embodiments, the elongated resilient support elements may be non-conductive.

The hinges (including the yarn and covering layers) may have any suitable thickness, for example, in the range of 10 to 140 microns.

The catheter apparatus may include one or more positions sensors, for example, a position sensor (e.g., a multi-axis sensor) disposed in the distal receptacle of the nose connector, and/or a position sensor (e.g., a single-axis sensor) disposed between the coupler and the pusher. A nose cap may be used to cover the distal facing opening of the nose connector.

SYSTEM DESCRIPTION

Reference is now made to FIG. 1, which is a schematic view of a basket catheter 10 constructed and operative in accordance with an embodiment of the present invention. The basket catheter 10 includes an elongated deflectable element 12 having a distal end 14, a coupler 16 connected to the distal end 14, and a pusher 18 including a distal portion 20. The pusher 18 is configured to be advanced and retracted through the deflectable element 12, for example, using a manipulator or handle (not shown). The basket catheter 10 also includes an expandable assembly 22 comprising a plurality of flexible polymer circuit strips 24 (only some labeled for the sake of simplicity). Each flexible polymer circuit strip 24 includes multiple electrodes 26 disposed thereon (only some labeled for the sake of simplicity). The formation of the various elements and how they are connected with each other are described in more detail with reference to the FIGS. 4-20.

Figure 2:
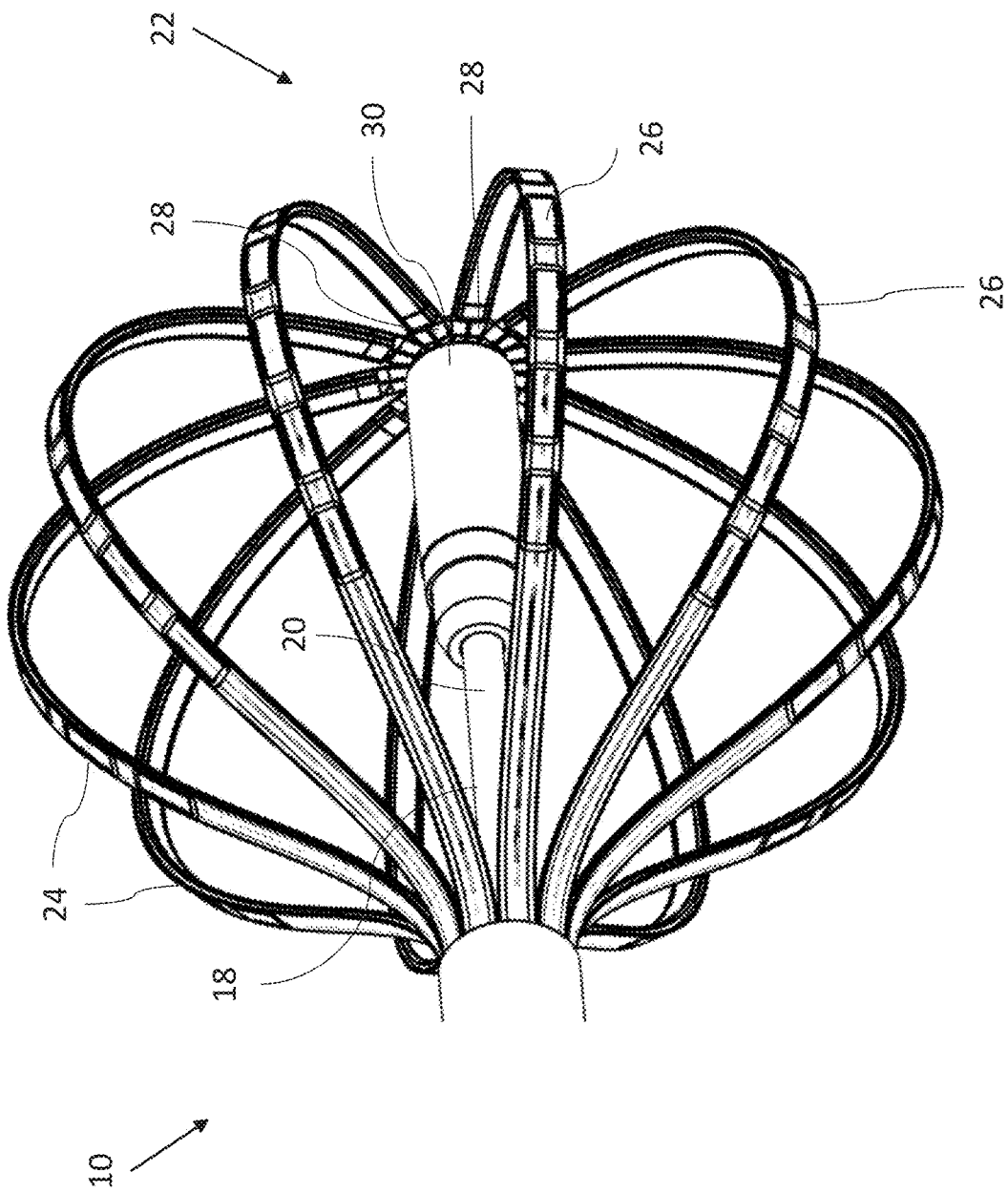
FIGS. 2 and 3 are more detailed views of the expandable assembly of the basket catheter of FIG. 1.
Figure 3:
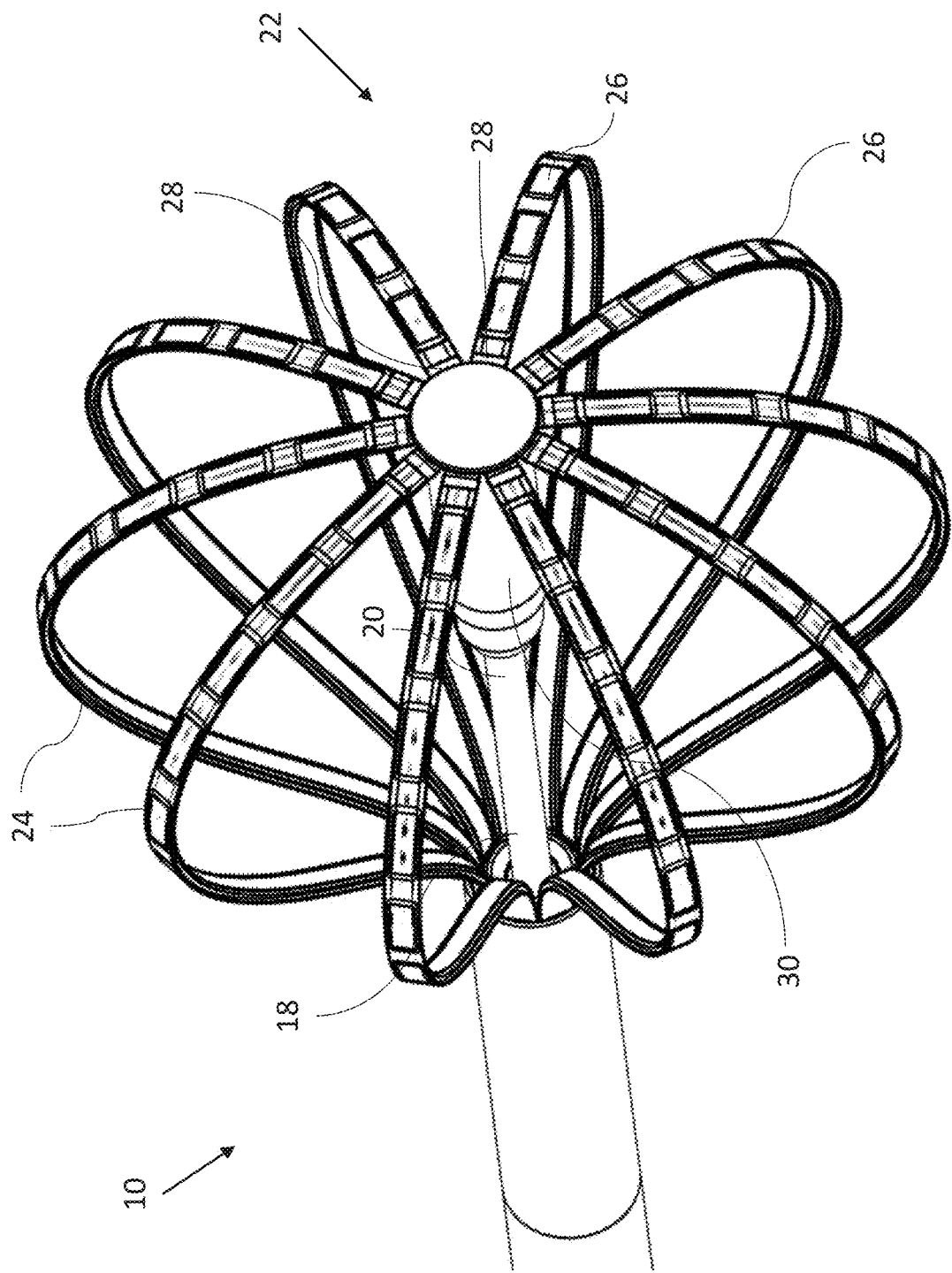

Reference is now made to FIGS. 2 and 3, which are more detailed views of the expandable assembly 22 of the basket catheter 10 of FIG. 1. FIGS. 2 and 3 show the electrodes 26 on the flexible polymer circuit strips 24 more clearly. FIG. 2 shows that the electrodes 26 are not disposed on the proximal portions of the flexible polymer circuit strips 24. The basket catheter 10 includes a nose connector 30 connected to the distal portion 20 of the pusher 18. The flexible polymer circuit strips 24 are connected via hinges 28 (only some labeled for the sake of simplicity) of the flexible polymer circuit strips 24 to the nose connector 30.

Figure 4:
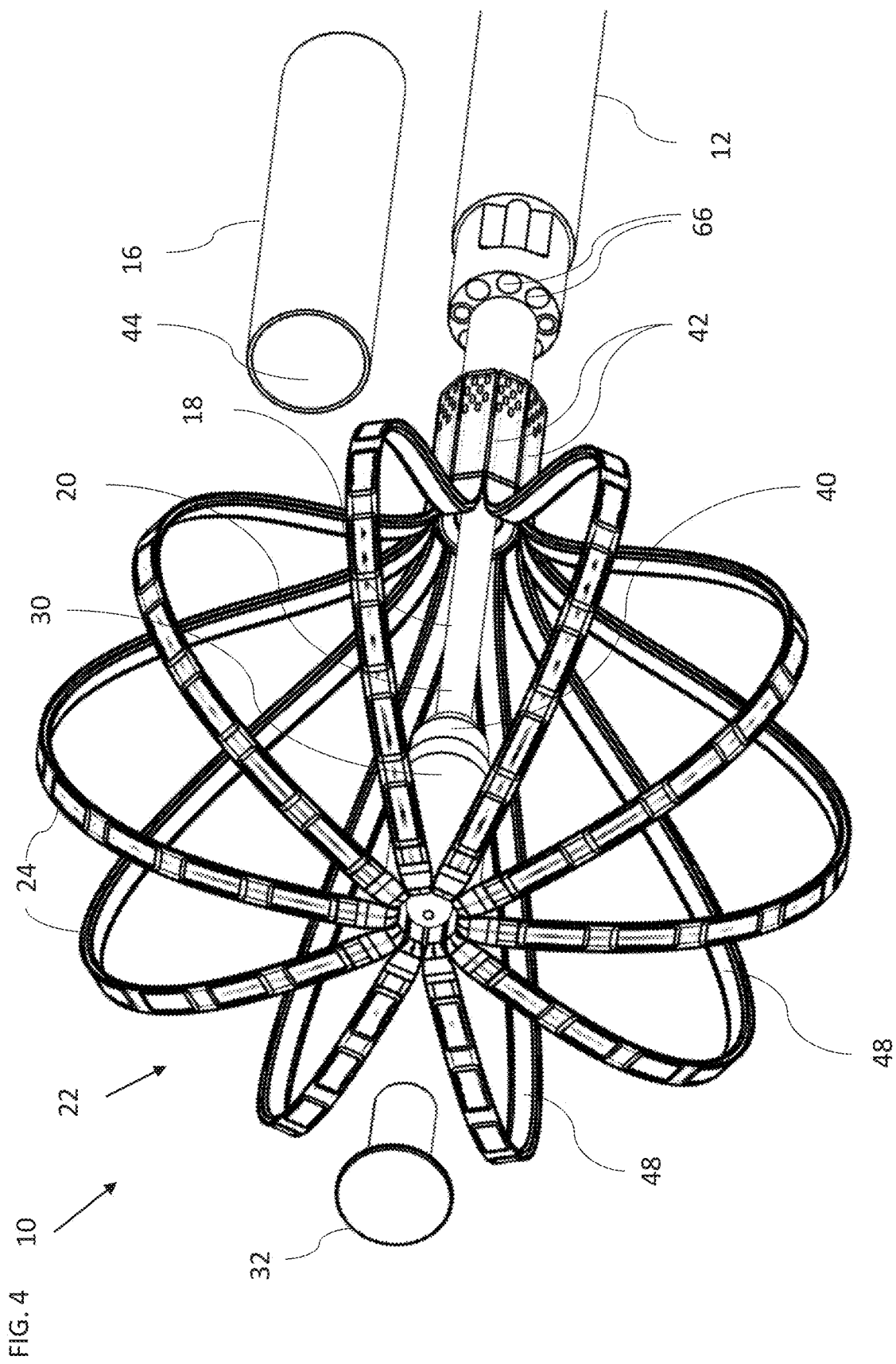
FIG. 4 is a partly exploded view of the basket catheter of FIG. 1.
Figure 5:
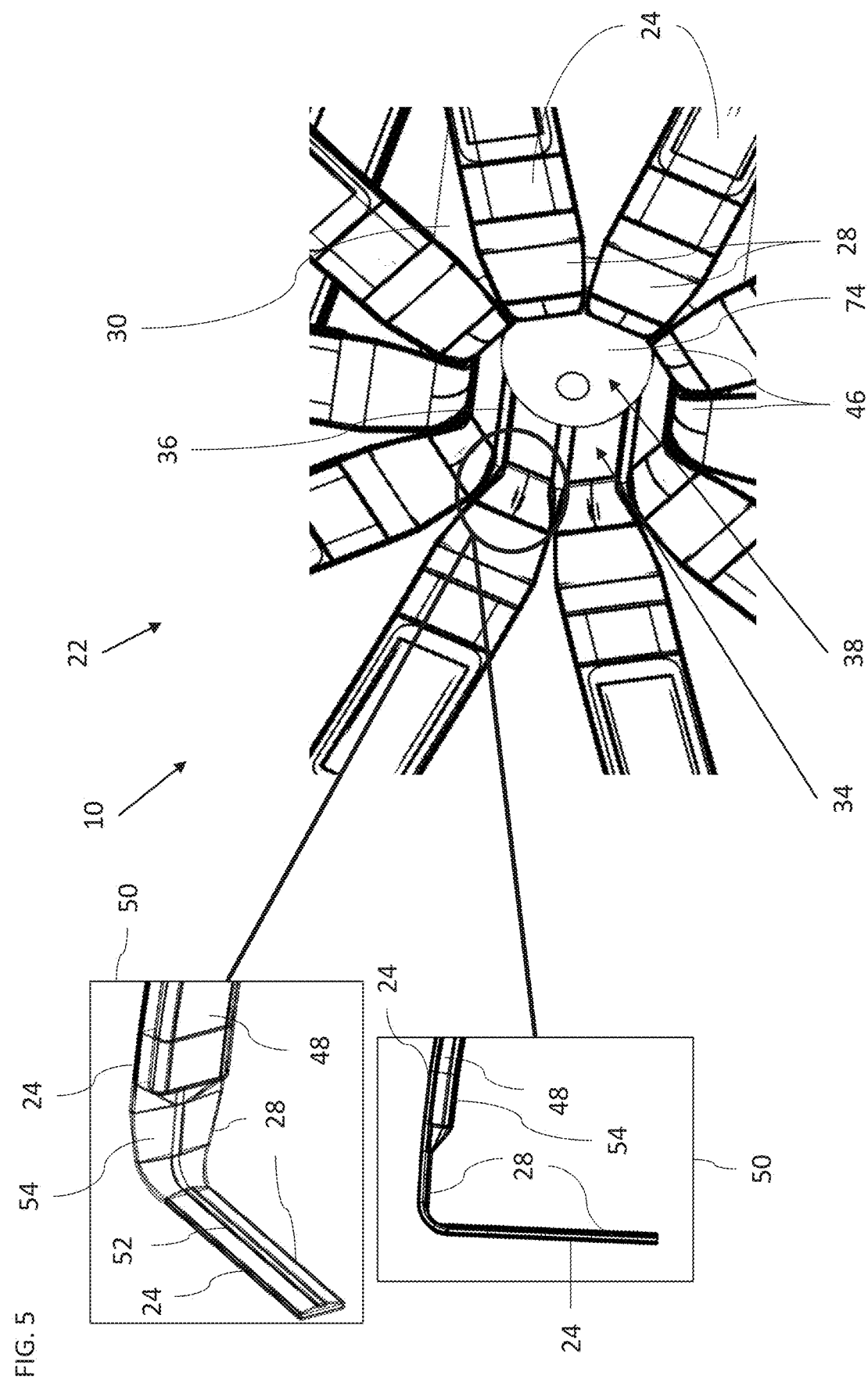
FIG. 5 is an enlarged view of a nose section of the basket catheter of FIG. 1 with a nose cap removed.

Reference is now made to FIGS. 4-5. FIG. 4 is a partly exploded view of the basket catheter 10 of FIG. 1. FIG. 5 is an enlarged view of a nose section of the basket catheter 10 of FIG. 1 with a nose cap 32 removed.

FIG. 4 shows the nose cap 32 and the coupler 16 removed from the basket catheter 10 to illustrate how the flexible polymer circuit strips 24 are connected to the nose connector 30 and the coupler 16. The nose connector 30 is connected to the distal portion 20 of the pusher 18. The proximal end of the coupler 16 may be connected to the elongated deflectable element 12 using any suitable connection method, such as using adhesive, for example, epoxy. The nose connector 30 is secured to the distal portion 20 of the pusher 18 using a center electrode ring 40, which is described in more detail with reference to FIGS. 14 and 19. The flexible polymer circuit strips 24 are disposed circumferentially around the distal portion 20 of the pusher 18, with first ends 42 (only some labeled for the sake of simplicity) of the strips 24 being connected to an inner surface 44 of the coupler 16. The connection between the flexible polymer circuit strips 24 and the inner surface 44 is shown more clearly with reference to FIG. 20.

FIG. 5 shows that the nose connector 30 includes a distal receptacle 34 having an inner surface 36 and a distal facing opening 38. The nose connector 30 is described in more detail with reference to FIGS. 13A-B and 19. FIG. 5 shows that second ends 46 (FIG. 5) (only some labeled for the sake of simplicity) of the strips 24 comprising the respective hinges 28 (FIG. 5) entering the distal facing opening 38 (FIG. 5) and are connected to the inner surface 36 (FIG. 5) of the distal receptacle 34 (FIG. 5) of the nose connector 30.

FIG. 4 shows that the basket catheter 10 also includes respective elongated resilient support elements 48 connected along a given length of respective ones of the flexible polymer circuit strips 24 providing a shape of the expandable assembly 22 in the expanded form of the expandable assembly 22. The elongated resilient support elements 48 may include any suitable material, for example, but not limited to, Nitinol and/or Polyetherimide (PEI).

FIG. 4 shows that the respective elongated resilient support elements 48 extend along inner surface of the respective strips 24 from the coupler 16, while FIG. 5 shows that the elongated resilient support elements 48 extend along the respective flexible polymer circuit strips 24 until before the respective hinges 28. Insets 50 of FIG. 5 show one of the hinges 28 and a portion of one of the flexible polymer circuit strips 24 adjacent to that hinge 28. The insets 50 illustrate that the elongated resilient support element 48 does not extend to the region of the hinge 28. It can also be seen that the hinge region is much thinner than the region including the elongated resilient support element 48. The hinges 28 may have any suitable thickness, for example, in the range of approximately 10 to approximately 140 microns. The strip 24 are folded such that strip 24 defines a generally perpendicular configuration (inset 50) to each other.

In some embodiments, each of the flexible polymer circuit strips 24 comprises a polyimide layer. The flexible polymer circuit strips 24 may be composed of any suitable materials. The flexible polymer circuit strips 24 are described in more detail with reference to FIGS. 7 and 8.

FIG. 5 also shows that respective ones of the second ends 46 of respective ones of the flexible polymer circuit strips 24 are tapered along the width of the respective ones of the flexible polymer circuit strips 24 to allow inserting the second ends 46 into the distal receptacle 34 without overlap. The hinges 28 may be connected to the inner surface 36 of the distal receptacle 34 using any suitable adhesive, for example, epoxy, and/or using any suitable connection method.

The hinges 28 of the flexible polymer circuit strips 24 are supported with a length of yarn 52, which typically runs the length of each respective flexible polymer circuit strip 24. Each flexible polymer circuit strip 24 along with the yarn 52 and the associated elongated resilient support element 48 may be covered with a suitable covering 54, e.g., thermoplastic polymer resin shrink wrap (PET) described in more detail with reference to FIG. 8. Yarn 52 can be any suitable high strength polymer including, for example, ultra high molecular weight polyethylene (Spectra or Dyneema), Kevlar, liquid crystal polymer (Vectran) and the like.

Reference is now made to FIGS. 6A and 6B, which are schematic views of the expandable assembly 22 of the basket catheter 10 of FIG. 1 in expanded and collapsed form, respectively. The flexible polymer circuit strips 24 are configured to bow radially outward when the pusher 18 is retracted expanding the expandable assembly 22 from a collapsed form to an expanded form. The collapsed form of the expandable assembly 22 represents the non-stressed form of the flexible polymer circuit strips 24 which are provided with their shape using the elongated resilient support elements 48 (FIG. 4).

In some embodiments, the flexible polymer circuit strips 24 are formed as flat strips as described in more detail with reference to FIG. 7. The distal ends of the flexible polymer circuit strips 24 are connected to the inner surface 36 (FIG. 5) of the nose connector 30 that the flat flexible polymer circuit strips and the nose connector are configured to cooperate together to define a flat distal tissue contacting region when the expandable assembly is in the expanded form. At that point the flat flexible polymer circuit strips 24 are generally parallel with a line 58, which is an extension of an axis of the nose connector 30 extended distally beyond the distal end of the nose connector 30. The proximal ends of the flexible polymer circuit strips 24 are then connected to the coupler 16 so that in the collapsed form, the angle between a tangent 56 to the flexible polymer circuit strips 24 and the line 58 is close to 180 degrees, while in the expanded form, the angle between the tangent 56 and the line 58 is about 90 degrees. Therefore, in operation (when the flexible polymer circuit strips 24 are connected to the nose connector 30 and the coupler 16) the hinges 28 are configured to provide a maximum angular range of movement of the flexible polymer circuit strips 24 of about 90 degrees and generally in excess of 80 degrees. However, the hinges 28 are capable of bending 180 degrees or more. The maximum angular range is defined as the maximum angular ramie between the tangent 56 to the flexible polymer circuit strips 24 and the line 58. The tangent 56 to the most distal portion of the flexible polymer circuit strips 24 generally provides the maximum angular range between the flexible polymer circuit strips 24 and the line 58.

Figure 7:
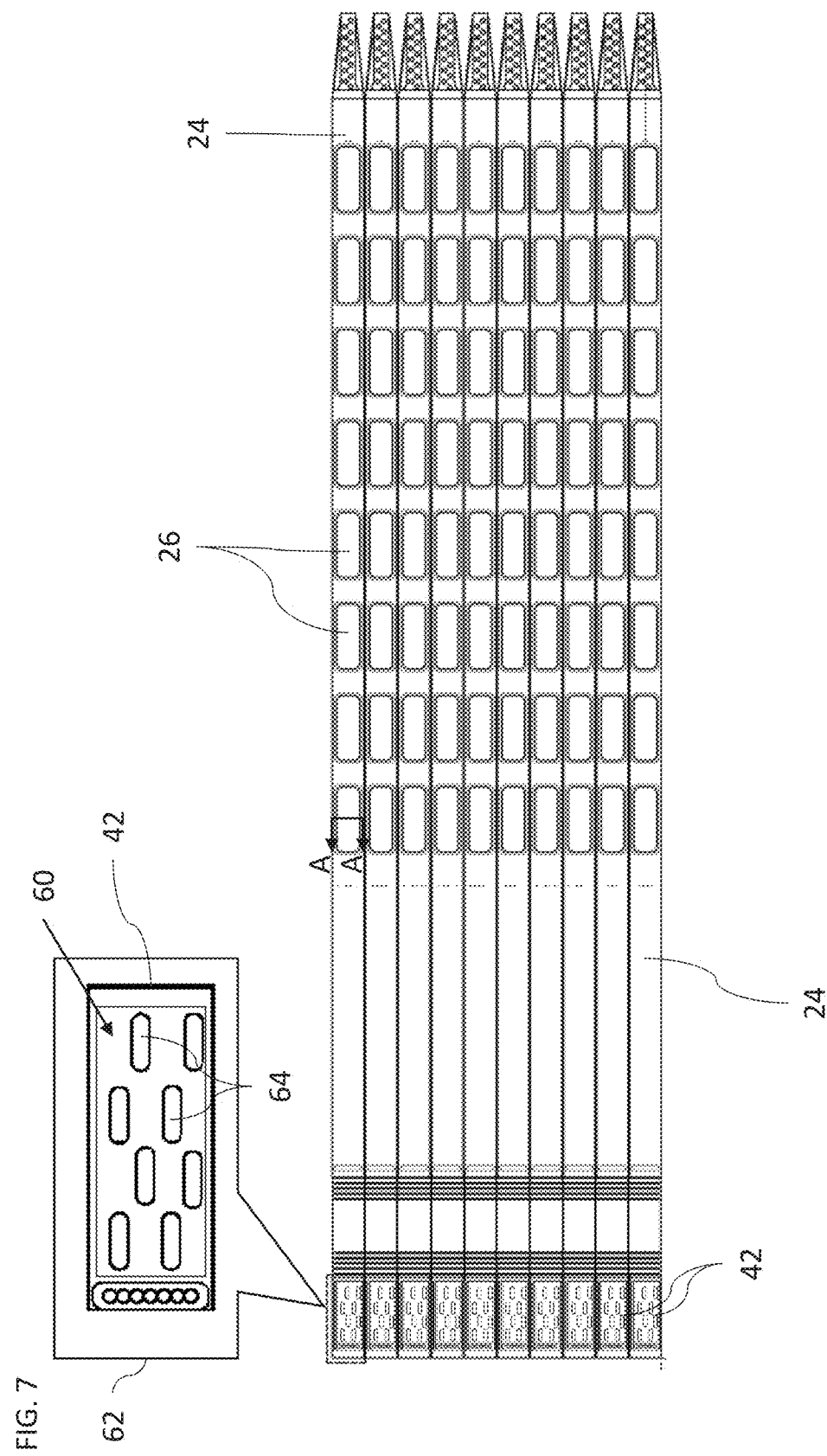
FIG. 7 is a schematic view of the flexible polymer circuit strips for use in the basket catheter of FIG. 1.

Reference is now made to FIG. 7, which is a schematic view of the flexible polymer circuit strips 24 for use in the basket catheter 10 of FIG. 1. The flexible polymer circuit strips 24 may be formed from a single piece of polymer, such as polyimide. Circuit strips 24 may be connected to each other by polyimide, or assembled as individual pieces that are held in proper alignment and secured to coupler 16. By manufacturing circuit strips 24 as individual components the yield of the base circuit may be increased as a failed electrode scraps one circuit strip rather than an entire assembly of strips. Respective first ends 42 of the respective flexible polymer circuit strips 24 include an electrical connection array 60. An inset 62 shows that the electrical connection array 60 includes electrical contacts 64 thereon (only some labeled for the sake of simplicity). The electrical contacts 64 are connected via traces (not shown) on the back of the flexible polymer circuit strips 24 to respective ones of the electrodes 26 disposed on the front of the flexible polymer circuit strips 24. Away from the region of the first ends 42, the flexible polymer circuit strips 24 are separate from each other to allow the flexible polymer circuit strips 24 to form the expandable assembly 22 (FIG. 1) when connected to the basket catheter 10. Wires (not shown) may connect the electrodes 26 to control circuitry (not shown) via the electrical contacts 64. The wires may be disposed in lumens 66 (FIG. 4) of the elongated deflectable element 12 (FIG. 4).

The flexible polymer circuit strips 24 may have any suitable dimensions. For example, the length of the flexible polymer circuit strips 24 may be in the range of 10 mm to 60 mm, e.g., 30 mm the width of the flexible polymer circuit strips 24 may be in the range of 0.25 mm to 3 mm, e.g., 0.72 mm, the thickness of the flexible polymer circuit strips 24 may be in the range of 0.005 mm to 0.14 mm.

Reference is now made to FIG. 8, which is a cross-sectional view through line A-A of FIG. 7. The yarn 52 is run along the length of the elongated resilient support element 48, e.g., formed from Nitinol or PEI, and beyond so that the yarn 52 will also run the length of the hinge 28 comprised of the flexible polymer circuit strips 24. The elongated resilient support elements 48 may have any suitable thickness, for example, in the range of 0.025 mm to 0.25 mm. A covering 68, such as a thermoplastic polymer resin shrink wrap (PET), is placed over the yarn 52 and the elongated resilient support element 48. Epoxy is injected into the covering 68. Heat is then applied to the covering thereby shrinking the covering over the yarn 52 and the elongated resilient support element 48. One reason to cover the elongated resilient support element 48 with the covering 68 is to electrically isolate the elongated resilient support element 48 from the circuit traces of the flexible polymer circuit strip 24. The covering 68 may be omitted, for example, if the elongated resilient support element 48 is covered with an insulating coating (e.g., polyurethane) or is comprised of an insulating material.

The flexible polymer circuit strip 24 are then placed over the yarn 52 and the elongated resilient support element 48 with the circuit trace side of the flexible polymer circuit strip 24 facing the elongated resilient support element 48 and the electrodes 26 of the flexible polymer circuit strips 24 facing away from the elongated resilient support element 48. The covering 54 is disposed around the flexible polymer circuit strip 24, yarn 52, and elongated resilient support element 48 combination, and epoxy 70 is injected into the covering 54. The covering 54 is then heated thereby shrinking the covering 54 around the combination. The flexible polymer circuit strips 24 are therefore covered with the covering 54, e.g., a thermoplastic polymer resin shrink wrap (PET).

The yarn 52 may comprises any one or more of the following: an ultra-high-molecular-weight polyethylene yarn; or a yarn spun from a liquid-crystal polymer. The yarn 52 may be any suitable linear density, for example, in a range between 25 denier and 250 denier.

Figure 20:
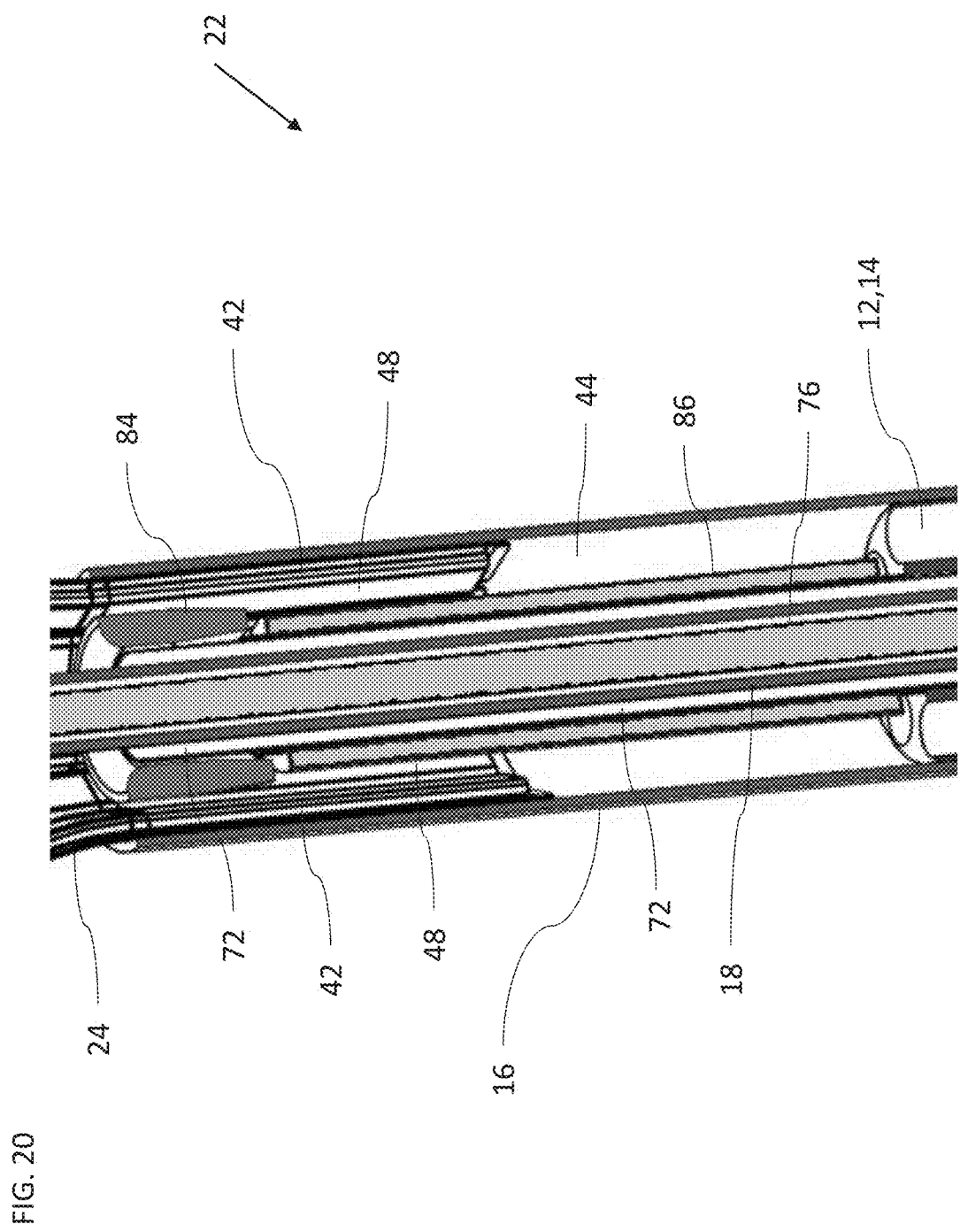

Reference is now made to FIG. 9, which is a schematic view of the elongated deflectable element 12 of the basket catheter 10 of FIG. 1. The elongated deflectable element 12 may be produced from any suitable material, for example, polyurethane or polyether block amide. The distal end 14 of the elongated deflectable element 12 has a smaller outer diameter than the rest of the elongated deflectable element 12 to accept the coupler 16 thereon as shown in FIG. 20. The elongated deflectable element 12 includes lumens 66 for inserting various tubes and wires therein as described herein. The elongated deflectable element 12 may have any suitable outer diameter and length, for example, the outer diameter may be in a range between 1 mm and 4 mm and the length may be in a range between 1 cm and 15 cm.

Reference is now made to FIG. 10, which is a schematic view of an irrigation sleeve 72 of the basket catheter 10 of FIG. 1. The irrigation sleeve 72 is a flexible tube which is disposed in one of the lumens 66 (FIG. 9) of the elongated deflectable element 12 (FIG. 9). The irrigation sleeve 72 may be used to carry irrigation fluid to the region of the expandable assembly 22 (FIG. 1). The irrigation sleeve 72 is sized to fit in one of the lumens 66 (typically a central lumen) of the elongated deflectable element 12 and extend beyond the distal end 14 (FIG. 9) of the elongated deflectable element 12 as shown in FIG. 20. The inner and outer diameter of the irrigation sleeve 72 may be in the range between 3 mm and 5 mm. The irrigation sleeve 72 may be formed from any suitable material, for example, but not limited to polyimide, polyurethane, polyether block amide, or polyethylene terephthalate.

Figure 19:
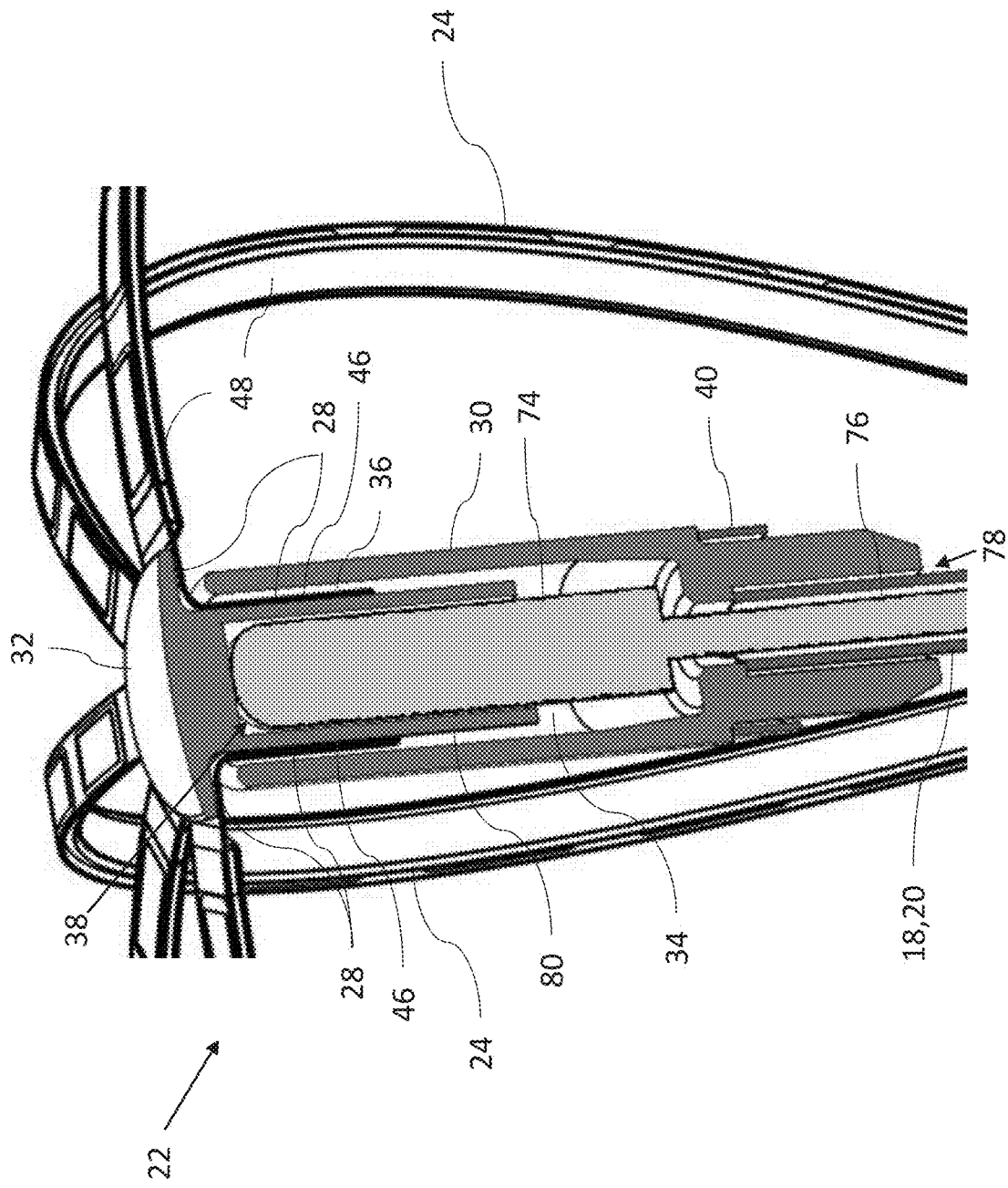
FIGS. 19-20 are cross sectional views through line A-A of FIG. 1.

Reference is now made to FIG. 11, which is a schematic view of the pusher 18 of the basket catheter 10 of FIG. 1. The pusher 18 is a flexible tube and is disposed in the irrigation sleeve 72. The pusher 18 is sized to slide in the irrigation sleeve 72 and allow room for irrigation fluid to pass between the irrigation sleeve 72 and the pusher 18. The inner diameter of the pusher 18 is sized to accommodate wiring of a multi-axis position sensor described with reference to FIG. 12. The pusher 18 extends beyond the distal end 14 of the elongated deflectable element 12 (FIG. 9) until the nose connector 30 as shown in FIG. 19. The pusher 18 may be formed from any suitable material, for example, but not limited to polyimide with or without braiding, polyether ether ketone (PEEK) with or without braiding, or polyamide with or without braiding.

Reference is now made to FIG. 12, which is a schematic view of a multi-axis position sensor 74 of the basket catheter 10 of FIG. 1. The multi-axis position sensor 74 may comprise a dual-axis or triple-axis position sensor, for example, a magnetic position sensor comprising multiple orthogonal coils. Wiring 76 is used to connect the multi-axis position sensor 74 via the hollow of the pusher 18 (FIG. 11) to a position computation system (not shown) disposed proximally to the basket catheter 10. The multi-axis position sensor 74 and the wiring 76 are shown in more detail in FIGS. 5 and 19.

Figure 13A:
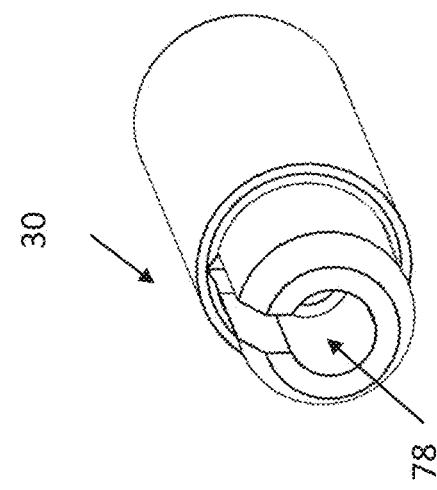
FIGS. 13A-B are schematic views of a nose connector of the basket catheter of FIG. 1.
Figure 13B:
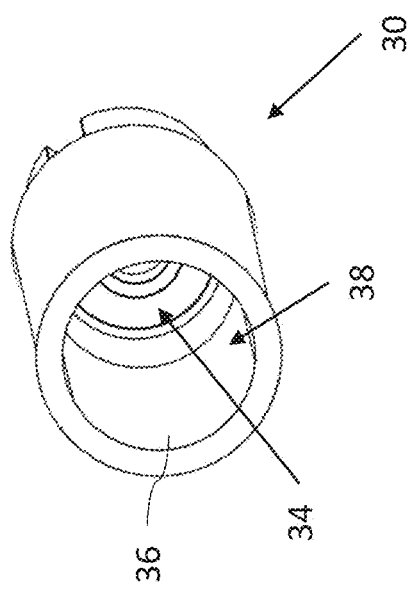

Reference is now made to FIGS. 13A-B, which are schematic views of the nose connector 30 of the basket catheter 10 of FIG. 1. The nose connector 30 may be formed from any suitable material, for example, but not limited to polycarbonate with or without glass filler, PEEK with or without glass filler, or PEI with or without glass filler. The nose connector 30 includes a proximal cavity 78 (FIG. 13A) in which the pusher 18 (FIG. 11) is secured and through which the wiring 76 passes as shown in FIG. 19. FIG. 13B also shows the distal receptacle 34, the inner surface 36, and the distal facing opening 38. The distal receptacle 34 houses the multi-axis position sensor 74 (FIG. 12) and the hinges 28 (FIG. 5) which are connected to the inner surface 36.

Figure 14:
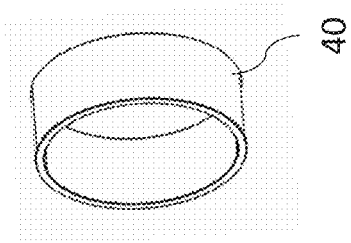
FIG. 14 is a schematic view of a nose connector retainer of the basket catheter of FIG. 1.

Reference is now made to FIG. 14, which is a schematic view of the center electrode ring 40 of the basket catheter 10 of FIG. 1. Electrode 40 is electrically connected to a wire (not shown) that passes through the slot in the side of proximal cavity 78 and into pusher 18. The center electrode ring 40 may be formed from any suitable material, for example, but not limited to noble metals and their alloys comprising platinum, palladium, gold, or iridium. The center electrode ring 40 serves a secondary role by providing mechanical support around the proximal cavity 78 (FIG. 13A) of the nose connector 30 to secure the nose connector 30 to the pusher 18 (FIG. 11) as shown in FIG. 19.

Figure 15A:
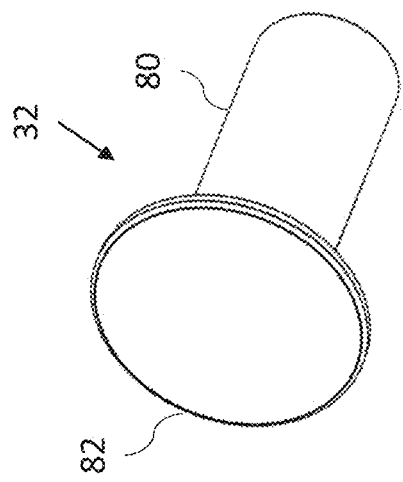
FIGS. 15A-B are schematic views of a nose cap of the basket catheter of FIG. 1.
Figure 15B:
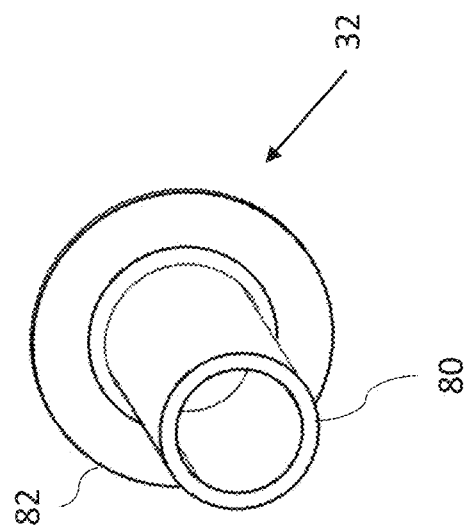

Reference is now made to FIGS. 15A-B, which are schematic views of the nose cap 32 of the basket catheter 10 of FIG. 1. The nose cap 32 includes a hollow cylinder 80 covered with a cover 82 which may be wider than the hollow cylinder 80. The nose cap 32 may be formed from any suitable material, for example, but not limited to polycarbonate with or without glass filler, PEEK with or without glass filler, or PEI with or without glass filler. The nose cap 32 is sized to fit in the distal receptacle 34 (FIG. 13B) of the nose connector 30 (FIG. 13B) and cover the distal facing opening 38 (FIG. 13B) while allowing space for the multi-axis position sensor 74 (FIG. 12) and the hinges 28 (FIG. 5) therein as shown in FIG. 19. The nose cap 32 may optionally be sized to provide a pressure fit against the hinges 28 to prevent the hinges 28 from being pulled away from the inner surface 36 (FIG. 13B) of the nose connector 30 (FIG. 13B). The nose connector 30 may also function to protect the multi-axis position sensor 74.

Figure 16:
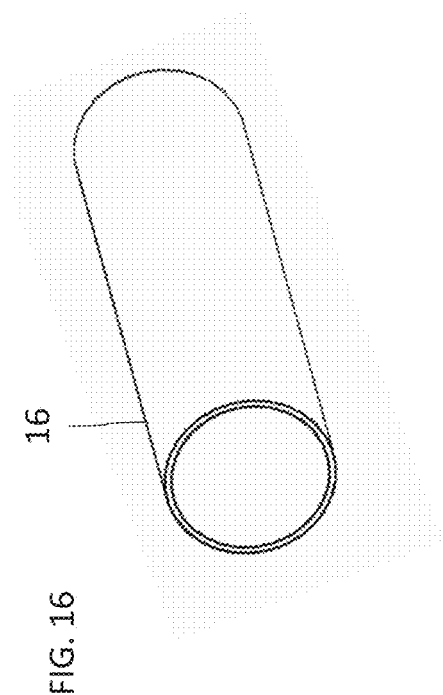
FIG. 16 is a schematic view of a coupler of the basket catheter of FIG. 1.

Reference is now made to FIG. 16, which is a schematic view of the coupler 16 of the basket catheter 10 of FIG. 1. The coupler 16 typically comprises a hollow tube and may be formed from any suitable material, for example, but not limited to polycarbonate with or without glass filler, PEEK with or without glass filler, polyimide, polyamide, or PEI with or without glass filler. The coupler 16 may be sized to have the same inner diameter as the outer diameter of the distal end 14 (FIG. 9) of the elongated deflectable element 12 (FIG. 9) and the same outer diameter as the proximal portion of the elongated deflectable element 12. The coupler 16 is also sized to surround various elements described in more detail with reference to FIG. 20.

Figure 17:
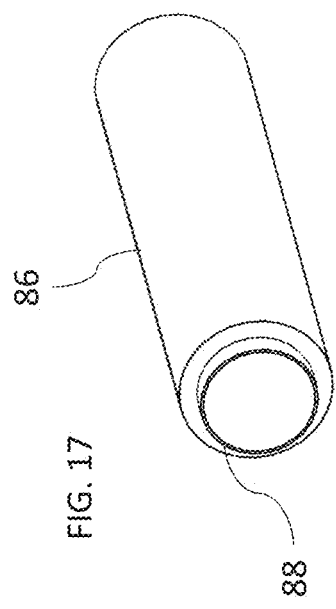
FIG. 17 is a schematic view of a single-axis position sensor of the basket catheter of FIG. 1.

Reference is now made to FIG. 17, which is a schematic view of a single-axis position sensor 86 of the basket catheter 10 of FIG. 1. The single-axis position sensor 86 may include any suitable position sensor, for example, a magnetic position sensor comprising a coil wound on a hollow cylinder 88. Wiring (not shown) from the single-axis position sensor 86 may be passed down one of the lumens 66 (FIG. 9) to a position computation system (not shown) disposed proximally to the basket catheter 10. The hollow cylinder 88 is sized to accommodate the irrigation sleeve 72 therein as shown in FIG. 20. The outer diameter and length of the single-axis position sensor 86 is sized to fit in the coupler 16 (FIG. 16). The hollow cylinder 88 may be formed from any suitable material, for example, but not limited to, a material used as a magnetic core.

Figure 18:
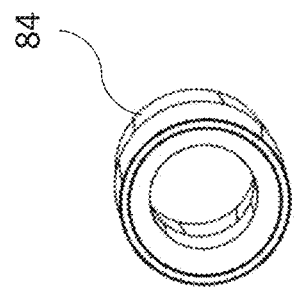
FIG. 18 is a schematic view of a proximal retainer ring of the basket container of FIG. 1.

Reference is now made to FIG. 18, which is a schematic view of a proximal retainer ring 84 of the basket container 10 of FIG. 1. The proximal retainer ring 84 is configured to provide a pressure fit around the distal end of the irrigation sleeve 72 (FIG. 10) and retain the single-axis position sensor 86 (FIG. 17) to be adjacent to the distal end 14 (FIG. 9) of the elongated deflectable element 12 (FIG. 9) as shown in FIG. 20. The proximal retainer ring 84 also serves to secure the flexible polymer circuits 24 between the retainer ring 84 and the coupler 16. The proximal retainer ring 84 may be formed from any suitable material, for example, but not limited to polycarbonate with or without glass filler, PEEK with or without glass filler, or PEI with or without glass filler.

Reference is now made to FIGS. 19-20, which are cross sectional views through line A-A of FIG. 1. FIG. 19 shows a distal portion of the expandable assembly 22, while FIG. 20 shows a proximal portion.

FIG. 19 shows that the distal portion 20 of the pusher 18 is disposed in the proximal cavity 78 of the nose connector 30 and is secured therein using the center electrode ring 40 disposed around the outside of the proximal cavity 78. The multi-axis position sensor 74 is disposed in the distal receptacle 34 of the nose connector 30 with the wiring 76 extending proximally through the pusher 18. The second ends 46 of the flexible polymer circuit strips 24 are connected to the inner surface 36 of the distal receptacle 34 of the nose connector 30. The elongated resilient support elements 48 extend along the length of the flexible polymer circuit strips 24 until, but not including, the hinges 28. The nose cap 32 is inserted into the distal receptacle 34 with the hollow cylinder 80 surrounding the distal portion of the multi-axis position sensor 74 and providing pressure against the second ends 46 of the flexible polymer circuit strips 24. The nose cap 32 covers the distal facing opening 38 of the nose connector 30.

FIG. 20 shows that the irrigation sleeve 72 is disposed in the elongated deflectable element 12. The pusher 18 is disposed in the irrigation sleeve 72. The wiring 76 is disposed in the pusher 18. The single-axis position sensor 86 is disposed around the irrigation sleeve 72 (between the coupler 16 and the pusher 18) close to the distal end 14 of the elongated deflectable element 12. The proximal retainer ring 84 provides a pressure fit around the irrigation sleeve 72 and keeps the single-axis position sensor 86 in place distally to the distal end 14 of the elongated deflectable element 12. The proximal end of the coupler 16 is connected to the distal end 14 of the elongated deflectable element 12. The first ends 42 of the flexible polymer circuit strips 24 are connected to the inner surface 44 of the coupler 16. FIG. 20 shows that the elongated resilient support elements 48 extend along the respective strips 24 from the coupler 16 until before the respective hinges 28 (FIG. 19).

While the expandable assembly is shown without being mounted to a flexible membrane, it is within the scope of the invention that the expandable assembly can be provided with a membrane (e.g., balloon like surface) as a base substrate for the circuit strips. As well, the membrane can be used as a covering layer over the circuit strips 24 with electrodes 26 being exposed (or not covered by the membrane for exposure) to the ambient environment (e.g., inside organ tissues). As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 72% to 108%.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and sub-combinations of the various features described hereinabove, as well as variations and modifications thereof which would occur to persons skilled in the art upon reading the foregoing description and which are not disclosed in the prior art.

What is claimed is:

1. A catheter apparatus, comprising:
   (a) an elongated deflectable element including a distal end;
   (b) a coupler connected to the distal end of the elongated deflectable element;

(c) a pusher including a distal portion, and being configured to be advanced and retracted through the deflectable element;

(d) a nose connector connected to the distal portion of the pusher, and including a distal receptacle including an inner surface and a distal facing opening;

(e) a position sensor coaxially located inside the nose connector; and (f) an expandable assembly comprising:

a plurality of flat flexible polymer circuit strips, each flat flexible polymer circuit strip including multiple electrodes disposed thereon, the flat flexible polymer circuit strips being disposed circumferentially around the distal portion of the pusher, with first ends of the flat flexible polymer circuit strips being connected to the coupler and second ends of the flat flexible polymer circuit strips comprising respective hinges angled inwardly and proximally in entering the distal facing opening and connected to the inner surface of the distal receptacle of the nose connector, the flat flexible polymer circuit strips being configured to bow radially outward when the pusher is retracted expanding the expandable assembly from a collapsed form to an expanded form such that the flat flexible polymer circuit strips and the nose connector are configured to cooperate together to define a flat distal tissue contacting region when the expandable assembly is in the expanded form, and a plurality of elongated resilient support elements, each extending along a respective one of the flat flexible polymer circuit strips and including a distal end proximal of a respective one of the hinges and a proximal end generally at a respective one of the first ends; and (g) a flat nose cap covering the distal facing opening of the nose connector, the nose cap including a cover and a cylinder, distal portions of the respective hinges subjected to a pressure fit between the cylinder and a distal portion of the nose connector, the flat distal tissue contacting region including the cover of the flat nose cap.

2. The apparatus according to claim 1, the respective hinges being configured to provide a maximum angular range of movement, which is in excess of 80 degrees, between the collapsed form and the expanded form.

3. The apparatus according to claim 1, the respective hinges having a thickness in the range of 10 to 140 microns.

4. The apparatus according to claim 1, the respective elongated resilient support elements including Nitinol.

5. The apparatus according to claim 1, the respective elongated resilient support elements including Polyetherimide (PEI).

6. The apparatus according to claim 1, the respective elongated resilient support elements extending along the respective flat flexible polymer circuit strips from the coupler until before the respective hinges.

7. The apparatus according to claim 1, the flat flexible polymer circuit strips comprising a polyimide layer.

8. The apparatus according to claim 1, the respective hinges of the flat flexible polymer circuit strips being supported with a length of yarn.

9. The apparatus according to claim 1, the flat flexible polymer circuit strips being covered with a thermoplastic polymer resin shrink wrap.

10. The apparatus according to claim 1, respective ones of the second ends of respective ones of the flat flexible polymer circuit strips being tapered along the width of the respective ones of the flat flexible polymer circuit strips.

11. The apparatus according to claim 1, the coupler including an inner surface, the first ends of the flat flexible polymer circuit strips being connected to the inner surface of the coupler.

12. The apparatus according to claim 1, respective ones of the first ends of respective ones of the flat flexible polymer circuit strips including an electrical connection array.

13. The apparatus according to claim 1, further comprising an electrode coaxially located around the periphery of the nose connector.

14. The apparatus according to claim 1, each hinge of the flat flexible polymer circuit strips being thinner than a bowing portion of the flat flexible polymer circuit strips.

15. A catheter apparatus, comprising (a) an elongated deflectable element including a distal end;

(b) a coupler connected to the distal end of the elongated deflectable element;

(c) a pusher including (i) a shaft including a distal portion, the shaft being configured to be advanced and retracted through the deflectable element, (ii) a position sensor secured to the distal portion of the shaft such that the position sensor is configured to translate longitudinally with the shaft relative to the deflectable element, and (iii) a wiring coupled with the position sensor, the wiring extending proximally from the position sensor and along the shaft such that wiring is configured to translate longitudinally with the shaft relative to the deflectable element;

(d) a nose connector connected to the distal portion of the pusher, and including a distal receptacle including an inner surface and a distal facing opening;

(e) an expandable assembly comprising:

a plurality of flexible polymer circuit strips, each flexible polymer circuit strip including multiple electrodes disposed thereon and a plurality of electrical contacts configured to communicate with a control circuit, each electrical contact of the plurality of electrical contacts being coupled with a respective electrode of the multiple electrodes, the flexible polymer circuit strips being disposed circumferentially around the distal portion of the pusher, with first ends of the strips being connected to the coupler and second ends of the strips comprising respective hinges angled inwardly and proximally in entering the distal facing opening and connected to the inner surface of the distal receptacle of the nose connector, the strips being configured to bow radially outward when the pusher is retracted expanding the expandable assembly from a collapsed form to an expanded form; and a plurality of elongated resilient support elements, each extending along a respective one of the flexible polymer circuit strips and including a distal end proximal of a respective one of the hinges and a proximal end generally at a respective one of the first ends; and (f) a flat nose cap covering the distal facing opening of the nose connector, the nose cap including a cover and a cylinder, the cylinder configured such that distal portions of the respective hinges are subjected to a pressure fit between the cylinder and a distal portion of the nose connector, and the nose cap configured such that the nose cap and the elongated resilient support elements together define a flat distal tissue contacting region.

16. The catheter apparatus of claim 15, further comprising an irrigation sleeve disposed in the elongated deflectable element.

17. A catheter apparatus, comprising:
(a) an elongated deflectable element including a distal end;
(b) a coupler connected to the distal end of the elongated deflectable element;
(c) a pusher including a distal portion, and being configured to be advanced and retracted through the deflectable element;
(d) an irrigation sleeve disposed in the elongated deflectable element, the pusher being configured to slide in the irrigation sleeve such that the pusher is slidably disposed within an interior region of the irrigation sleeve and the irrigation sleeve is positioned exteriorly to the pusher;
(e) a nose connector connected to the distal portion of the pusher, and including a distal receptacle including an inner surface and a distal facing opening;
(f) an expandable assembly comprising:
a plurality of flexible polymer circuit strips, each flexible polymer circuit strip including multiple electrodes disposed thereon, the flexible polymer circuit strips being disposed circumferentially around the distal portion of the pusher, with first ends of the strips being connected to the coupler and second ends of the strips comprising respective tapered hinges angled inwardly and proximally in entering the distal facing opening and connected to the inner surface of the distal receptacle of the nose connector without overlap, the strips being configured to bow radially outward when the pusher is retracted expanding the expandable assembly from a collapsed form to an expanded form such that the flexible polymer circuit strips and the nose connector are configured to cooperate together to define a flat distal tissue contact region when the expandable assembly is in the expanded form; and
a plurality of elongated resilient support elements, each extending along a respective one of the flexible polymer circuit strips and including a distal end proximal of a respective one of the hinges and a proximal end generally at a respective first end.

* * * * *